(12) United States Patent
Clemente

(10) Patent No.: US 8,517,991 B2
(45) Date of Patent: Aug. 27, 2013

(54) DRIVE SYSTEM FOR USE WITH AN INSULIN DELIVERY DEVICE

(75) Inventor: Matthew Clemente, King of Prussia, PA (US)

(73) Assignee: Animas Corporation, West Chester, PA (US)

( * ) Notice: Subject to any disclaimer, the term of this patent is extended or adjusted under 35 U.S.C. 154(b) by 101 days.

(21) Appl. No.: 12/751,618

(22) Filed: Mar. 31, 2010

(65) Prior Publication Data
US 2010/0249706 A1 Sep. 30, 2010

Related U.S. Application Data

(60) Provisional application No. 61/165,163, filed on Mar. 31, 2009.

(51) Int. Cl.
*A61M 5/14* (2006.01)

(52) U.S. Cl.
USPC .............................. 604/154; 604/131; 604/135

(58) Field of Classification Search
USPC ................. 604/121, 131, 134–136, 151–152, 604/154–155, 218, 246; 128/DIG. 12
See application file for complete search history.

(56) References Cited

U.S. PATENT DOCUMENTS

| | | | |
|---|---|---|---|
| 5,637,095 A * | 6/1997 | Nason et al. | 604/135 |
| 5,957,889 A | 9/1999 | Poulsen et al. | |
| 6,159,161 A * | 12/2000 | Hodosh | 600/561 |
| 6,537,251 B2 * | 3/2003 | Klitmose | 604/135 |
| 7,736,344 B2 | 6/2010 | Moberg et al. | |
| 2002/0004651 A1 * | 1/2002 | Ljunggreen et al. | 604/218 |
| 2008/0097381 A1 | 4/2008 | Moberg et al. | |
| 2009/0105650 A1 * | 4/2009 | Wiegel et al. | 604/152 |

FOREIGN PATENT DOCUMENTS

| | | |
|---|---|---|
| WO | WO 02/28455 A1 | 4/2002 |
| WO | WO 02/28456 A1 | 4/2002 |
| WO | WO 02/45780 A2 | 6/2002 |

OTHER PUBLICATIONS

European Search Report for EP 10 25 0664 Date of Mailing Sep. 9, 2010.
European Search Report for EP 10 25 0664.9-2320 Date of Mailing Jul. 17, 2012.

* cited by examiner

*Primary Examiner* — Quynh-Nhu H Vu
(74) *Attorney, Agent, or Firm* — Wayne C. Jaeschke, Jr.

(57) ABSTRACT

The invention relates to a mechanical drive system for a medical infusion device. The disclosed drive system employs a flexible tape with recesses or holes that are configured to mate with tabs or protrusions on a gear to advance the rotation of the gear at a rate determined by the pattern of recesses or holes on the flexible tape.

1 Claim, 11 Drawing Sheets

DRIVE SYSTEM FOR USE WITH AN INSULIN DELIVERY DEVICE

BACKGROUND OF THE INVENTION

This invention relates generally to improvements in liquid infusion devices of the type used for controlled administration of medication to a patient. More specifically this invention relates to an improved medication infusion device having a space-efficient drive system.

Infusion devices are well known in the art for use in delivering medication, such as insulin to a patient. U.S. Pat. No. 5,637,095 titled 'Medication infusion pump with flexible drive plunger' includes a compact drive motor mechanically coupled by a flexible drive member to a sliding piston for delivering medication to a patient. The flexible drive member extends through a space-efficient curved path, and comprises a length of spring tape formed from spring steel to have a curved cross sectional shape when oriented in linear configuration. The spring tape is wrapped or coiled onto a take-up spool within the pump housing. Drive means may be a lead screw nut carried on an elongated lead screw, with the drive motor providing a rotary output for driving the lead screw in a manner to advance the lead screw nut along the lead screw. Linear displacement of the lead screw nut translates the spring tape along its curved path. Or preferably a capstan roller and associated pinch roller engage and advance the spring tape under control of the pump drive motor, with a length of the spring tape loosely suspended and guidably-received within a curved path at one side of the drive means. In operation, when a medication-containing barrel is loaded into the pump housing, the pinch roller is retracted relative to the capstan roller to permit the tape to be inserted into or removed from the space between these rollers.

U.S. Pat. No. 6,537,251 titled 'Medication delivery device with bended piston rod' describes a flexible piston rod consisting of two separate tape-shaped bodies, joined together at one or more points, optionally describing an 'eye-shaped' path when viewed in a transversal cross-section in a relaxed state. Movement of the piston rod is activated by an electro-motor whose rotational movement is transferred to a linear displacement of the piston rod by suitable driving means, comprising a driving wheel. Said driving wheel including regularly spaced protrusions that interact with corresponding receiving members on the flexible piston rod (optionally isolated through-holes or slots) to displace the piston rod. In one embodiment, the piston rod is bent to make a 180 degrees U-turn over a first guiding wheel, and a second guiding wheel ensures proper contact between the piston rod and the driving wheel. In the longitudinal direction, the smallest diameter of the wheel is limited by the smallest diameter around which the rod may be elastically bent.

U.S. Pat. No. 5,957,889 titled 'Displacement system for controlled infusion of a liquid' describes a liquid displacement system having a piston rod as a flexible incompressible construction which is guided by a piston rod guide behind the rear end of the cartridge deflected away from the axis of the cartridge, preferably 180 degrees. The guide includes a track elaborated to the very shape which the curved part of the piston rod will spontaneously adopt when it's end portions are kept parallel, enabling the length of the device to be reduced to correspond to about the length of the cartridge and the deflecting piston rod guide. The flexible rod may be a flexible helix with narrowly adjacent turns of windings, and a coiling ratio within certain limits. The windings of the helix present an external thread which may be engaged by an internally threaded nut element which, when rotated, will drive the piston rod into the cartridge in conjunction with a presser foot acting on the free end of the piston rod.

The aforementioned, and other prior art presents many problems to be overcome. For example, locating the drive system relatively far from the plunger typically requires a thick piston rod that may require a high power consuming motor, possibly introducing inaccuracies in the displacement of the piston. Also, systems including several components such as drive wheels, take-up spools and additional supports or guides for the path of the tape whilst outside of the cartridge, lead to complex systems that may be more difficult to use and manufacture, whilst potentially introducing inaccuracies in the regulation of liquid infusion due to mechanical friction or component wear for example. Pumps including a cartridge typically require at least one dimension to be greater than twice the length of the cartridge in order to provide enough space for a piston rod to be fully retracted when a new, full cartridge is present. The invention disclosed herein provides a space-efficient drive system for a liquid infusion device.

SUMMARY OF THE INVENTION

The present invention provides a liquid infusion device that is discrete and easy for a patient to use. Combining the advantages of a piezoelectric motor and geared drive shaft that operate at the nano-scale level, with a flexible drive tape in a re-usable hub provides a space efficient system and method for administering liquid medication to a patient.

A compact profile is achieved using a cartridge with substantially elliptical geometry configured to removably attach to the reusable hub. The hub comprises a plunger driven by a flexible drive tape that cooperates with a geared drive shaft positioned at the base of the cartridge driven by a piezoelectric motor. A first end of the flexible drive tape is adapted to fix to the plunger whilst a second end assumes a space efficient path, wrapping around the drive shaft to take up a position between the cartridge and the reusable hub housing of the infusion device. The system profile has a length approximately equal to the length of a cartridge, plus the thickness of the drive tape, plus the diameter of the drive shaft (approximately equal to half the smallest diameter of the cartridge). Such a drive configuration allows use of larger capacity cartridges with minimal or no impact on the overall profile of the pump system.

The flexible drive tape comprises a striated polymer, flexible in a longitudinal direction and rigid in an axial direction, supported by rubber strips along its edges that interact with the cartridge geometry by gliding against the inner walls of the cartridge body at its widest diameter. The substantially elliptical geometry of the cartridge provides a single channel at its widest diameter through which the plunger and drive tape have restricted travel. Cooperation of tiny holes in the drive tape spaced nanometers apart, with a geared drive shaft and piezoelectric motor provides tight dosage regulation, enabling increments in the range 0.00005 to 0.0002 units, preferably more closer to 0.0001 units. Dose regulation is also unaffected by the size of the cartridge used.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

FIG. 3b is a bottom plan view of the pump of FIGS. 2 and 3a;

DETAILED DESCRIPTION OF ILLUSTRATIVE EMBODIMENTS OF THE INVENTION

While preferred embodiments of the present invention have been shown and described herein, it will be obvious to those skilled in the art that such embodiments are provided by way of example only. Numerous variations, changes, and substitutions will now occur to those skilled in the art without departing from the invention.

Figure 1:
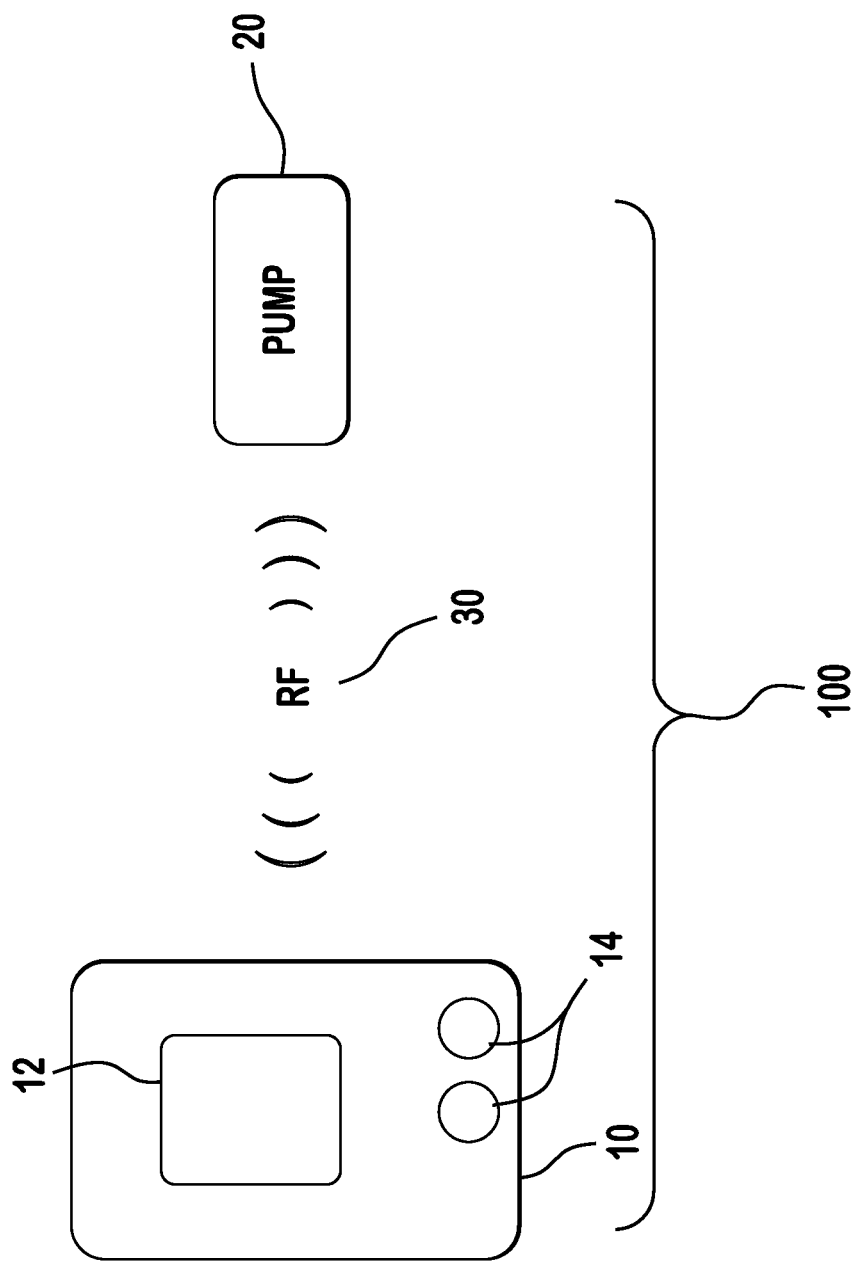
FIG. 1 is a simplified schematic view of the main components of a liquid infusion system.

FIG. 1 is a simplified schematic view of the main components of a liquid infusion system 100 for use with an embodiment of the present invention, including a pump 20, a handheld device 10 with a display 12, buttons 14 and wireless communication therebetween such as radio frequency (RF) 30.

Pump 20 may be any type of liquid infusion device such as an insulin-dosing pump for example, that may be worn by a patient attached to clothing or belt. Alternatively, pump 20 may be a small patch pump designed specifically to be worn attached to the skin of a patient whereby medication is provided to the patient via an infusion set. Pump 20 may be configured to communicate wirelessly with handheld device 10 in order to determine and optionally program a defined quantity of insulin to be infused to the patient.

Reference will be made herein to the treatment of diabetes by infusion of insulin by way of a small patch pump, however it would be apparent to a person skilled in the art that the present invention may be applicable to any type of liquid infusion device, as well as in the treatment of conditions other than diabetes, and is not intended to be limited to the example described herein.

In one example embodiment, the patient may use the interface of handheld device 10 to manage their condition, optionally including instructing the pump 20 to infuse a quantity of medication. Such interaction between the handheld device 10 and pump 20 may be via wireless communication such as RF 30 or Bluetooth for example. Handheld device 10 may incorporate an OLED display interface 12 including several buttons 14 or optionally it may utilize alternative methods such as a touch screen display for example. Handheld device 10 may additionally function as an analyte monitoring device such as a blood glucose measuring meter for example. Most operational features of the liquid infusion system 100 are likely to be contained within the handheld device 10 providing greater flexibility in design and allowing for additional features, such as software upgrades for example to be incorporated.

A user may either instruct the pump 20 to immediately dose a certain quantity of insulin, or alternatively they may program the pump 20 to dose a predefined volume of insulin at a predetermined time using the handheld device 10. Diabetic patients typically perform blood glucose tests several times a day and in particular at a predefined time both before and after a meal to ensure their blood sugar levels are kept in check. Depending on the measurement result, the patient may choose to dose him or herself with a certain quantity of insulin. Some patients inject the insulin into their thigh or stomach using a conventional needle and syringe or a pen-style device. However wearers of an infusion pump can be relieved from having to perform numerous separate injections as the pump may be worn constantly attached to the skin via an infusion set. The user may simply program the quantity of insulin to be infused using the hand-held device 10, which then communicates wirelessly with the pump 20 instructing it to deliver the correct dose of insulin.

Figure 2:
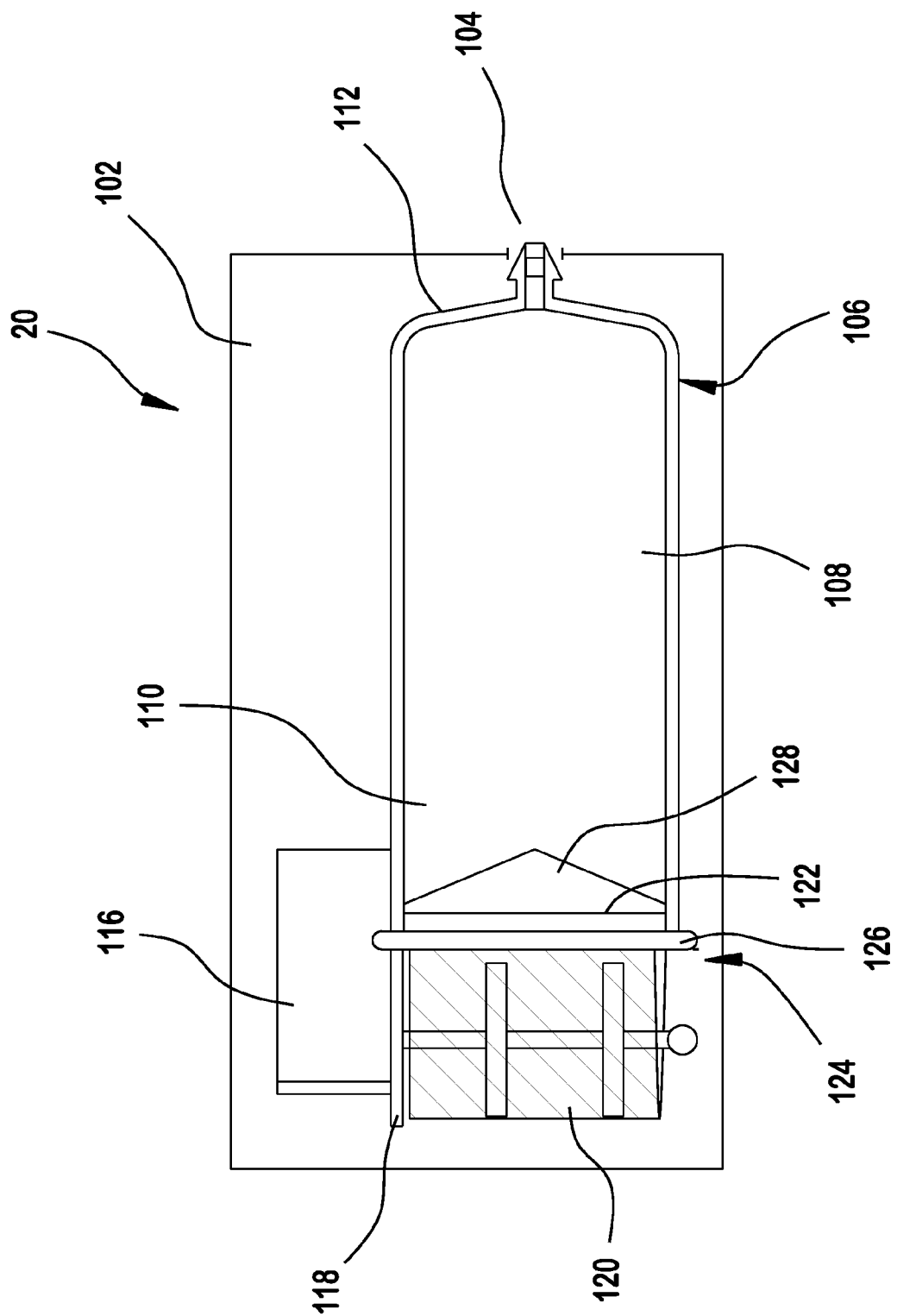
FIG. 2 is a top plan view of a pump according to the present invention.

FIG. 2 is a top plan view of an example embodiment of a simplified liquid infusion pump 20 according to the present invention, including a reusable hub housing 102 with an opening 104 and a cavity 106 to receive a cartridge 108. Cartridge 108 includes a proximal end 110 and a distal end 112, and a plunger 128 located close to proximal end 110 in this view. Housing 102 further includes a groove or recess 124 to receive a lip element 126 of the cartridge 108. According to the present invention, infusion pump 20 further includes a motor 116, a geared drive shaft 118, a flexible drive tape 120 and a cap 122.

The term 'cartridge' is used herein to describe a vial containing a medicinal liquid such as insulin for example, however other terms such as 'syringe', 'ampule' or 'carpule' for example may also be used interchangeably.

In one embodiment, liquid infusion pump 20 may comprise a reusable hub housing 102 formed by a hard piece of molded plastic for example, including a cavity or recess 106 designed specifically to receive a cartridge 108. Reusable hub housing 102 is configured to securely attach to the removable and replaceable cartridge 108. Cartridge 108 slots into the cavity or recess 106 within the hub housing 102 until a lip 126, located at the proximal end 110 of the cartridge 108, snaps into a cooperating groove 124 located in the hub housing 102 thereby securing the cartridge 108 to the hub housing 102. Once the cartridge is in place, motor 116 functions to advance the flexible drive tape 120 until the plastic cap 122 snaps into the cooperating plastic plate 127 (shown in FIG. 3) of the plunger 128. Optionally, a small force sensor (not shown) may be located on or integrated with the cap 122 to sense forces applied to the cap 122 and hence control operation of the drive motor 116. Once inserted correctly, cartridge 108 completely fills the recess 106 and the distal end 112 of the cartridge 108 locates close to the opening 104 in the hub housing 102 to allow connection of the dispensing tip 154 to an infusion set.

Motor 116 may be powered by a small battery, for example a small lithium button or coin shaped battery, or a coupling of batteries. Examples of battery models include CR1225, CR2450, CR2032 and BSR45L (silver oxide) available from Energizer for example. The battery may be sealed in a separate compartment to allow the user easy access in order to replace a spent battery.

During use, the user would access the pump to remove a spent cartridge and replace it with a new, full one. The pump would include an access hatch (not shown) specifically for this purpose. Upon opening the hatch, the user would grip the cartridge and lift it out of cavity 106. As the cartridge 108 is released, lip element 126 undocks from cooperating recess 124 and plunger 128 becomes disengaged from cap 122, which is permanently attached to the flexible drive tape 120. The new cartridge is then placed into cavity 106, allowing lip 126 to engage or 'click' into place within recess 124. Cap 122 may engage with plunger 128 either immediately as the user presses cartridge 108 into position, or alternatively cap 122 may be driven to engage with the plunger 128 on activation of the motor 116. The process of replacing the cartridge is therefore simple and intuitive and does not require the user to interact with any of the components of the reusable hub housing 102.

Figure 3A:
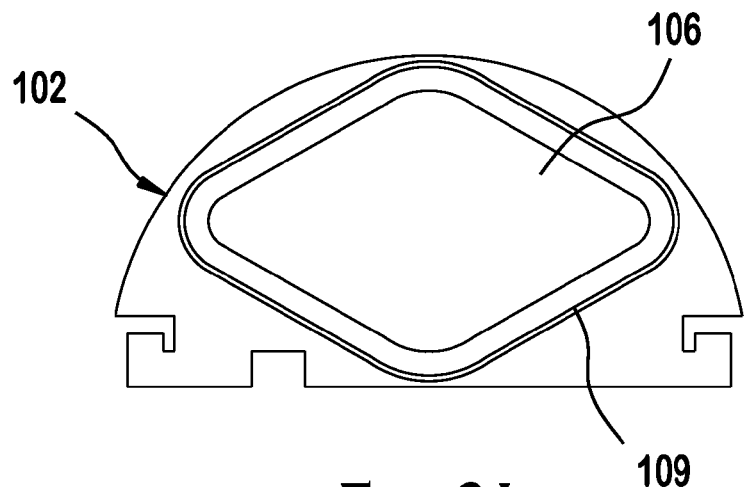
FIG. 3a is an end-on cross-sectional view of the reusable hub housing of FIG. 2.
Figure 6:
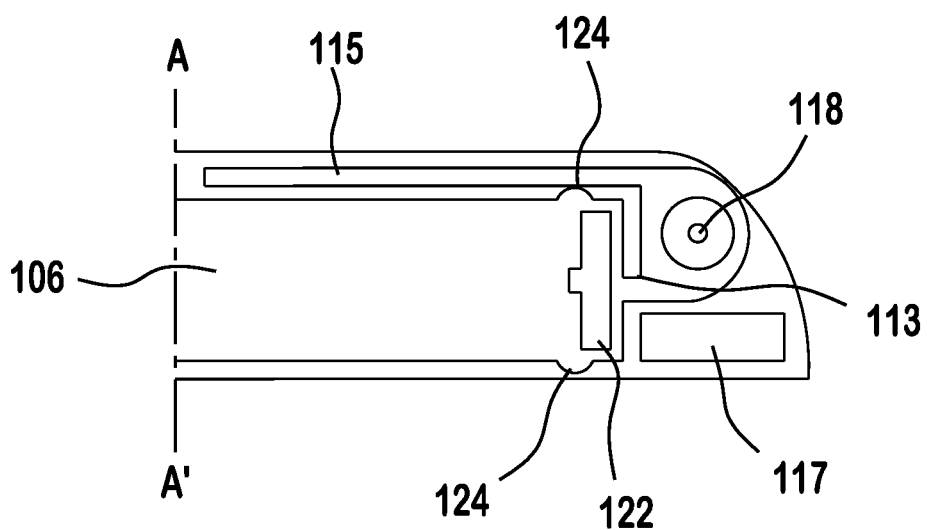
FIG. 6 is a side plan view of the reusable hub housing of FIGS. 2, 3 and 5.

FIG. 3a shows an end on cross-sectional view of an exemplary embodiment of the reusable hub housing 102 of FIG. 2, including cavity or recess 106 to accommodate a cartridge 108. FIG. 6 also includes a rubber seal 109, such as a commonly used 'O'-ring type seal.

Figure 3B:
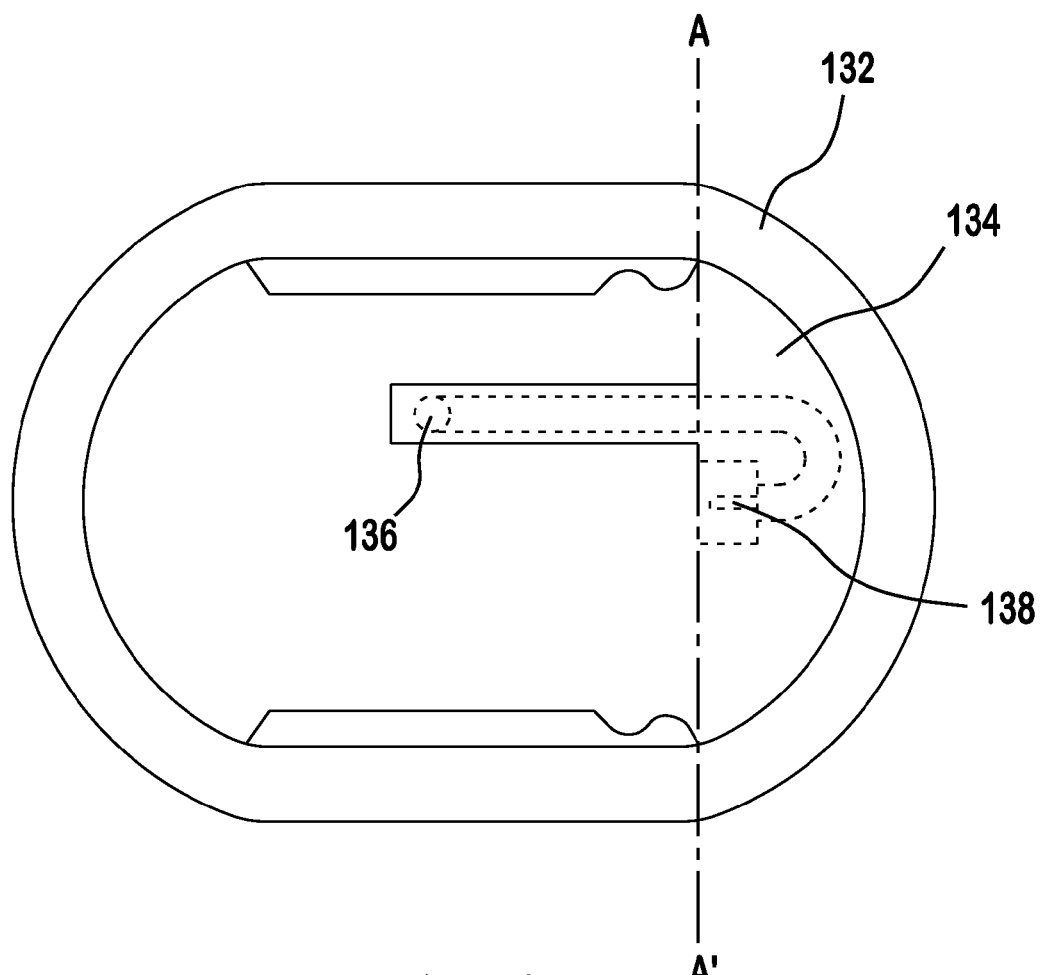

FIG. 3b shows a bottom plan view of the pump of FIGS. 2 and 3a. In one embodiment pump 20 may be a small 'patch' like device worn discretely on the skin of the user. FIG. 3b includes an adhesive tape 132, a plastic shell 134, a flexible cannula 136 and a needle 138 that pierces the silicone plug 156 at the dispensing tip 154 of the cartridge 108, as shown and described in relation to FIG. 4. FIG. 3b also shows a plane A-A' depicting the position of the distal end 112 of the cartridge 108. The location of plane A-A' is also depicted in FIGS. 5 and 6.

Referring now to FIGS. 3a and 3b, reusable hub 102 may form part of a compact insulin-dispensing pump 30 such as a patch pump for example, and the present discussion will focus on this embodiment. Pump 20 may be worn attached to the skin of a user using a suitable adhesive 132. When a full cartridge 108 of insulin is placed within pump 20, opening 104 is capped by the needle 138 of the underlying infusion set through which the medicinal liquid is infused to the patient via the flexible cannula 136. Plastic shell 134 enables the infusion set to snap easily into a cooperating inset in the reusable hub 102, ensuring that the external surfaces of the patch pump 20 are flush and hence not adding to the overall dimensions of the pump 20. However, as would be apparent to a person skilled in the art, the reusable hub and novel drive system of the present invention may be used with any form of medicinal liquid dispensing device and is not intended to be limited in any way to one particular type of pump.

Figure 4:
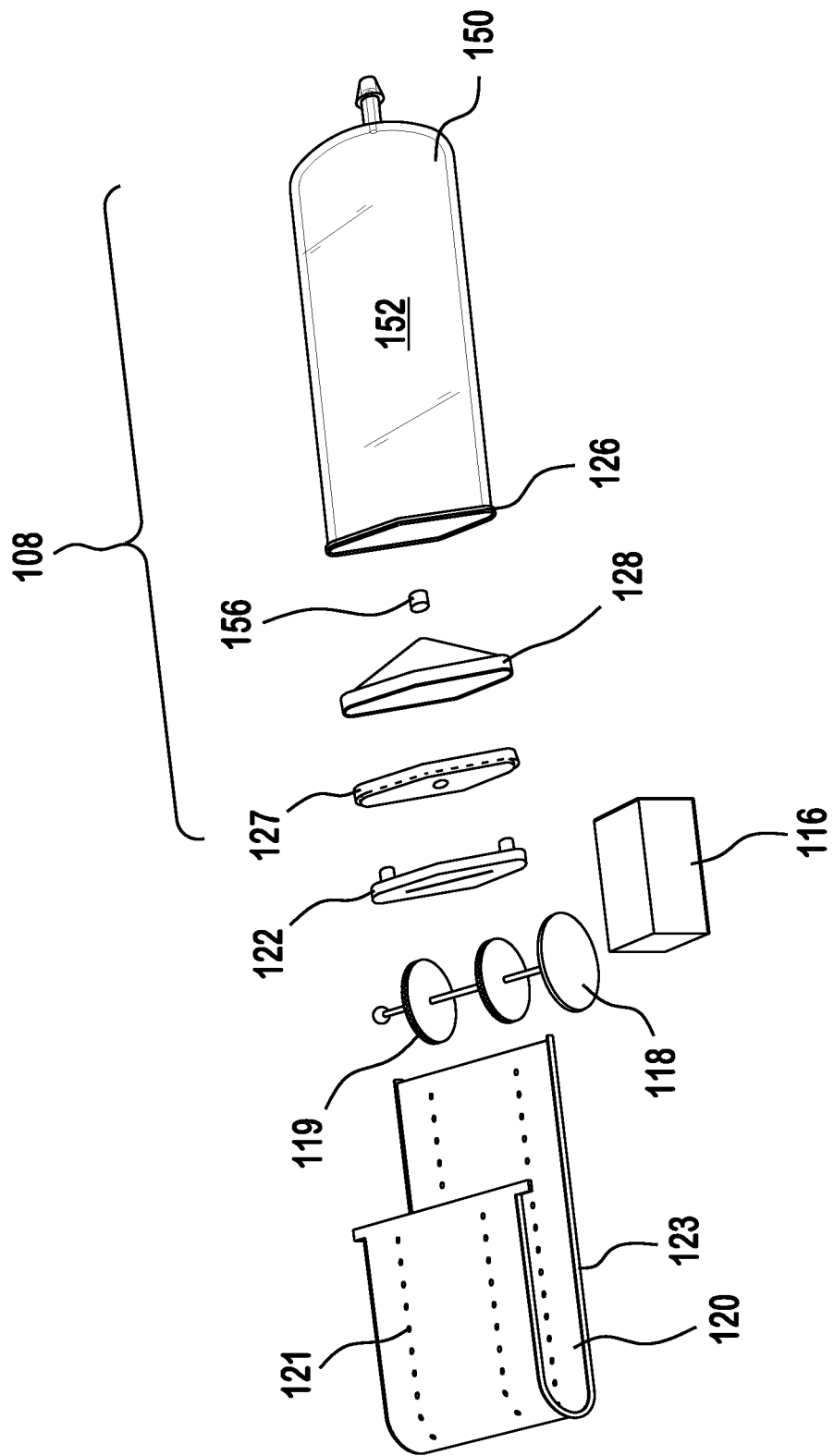
FIG. 4 is an exploded perspective view of the pump of FIG. 2.
Figure 5:
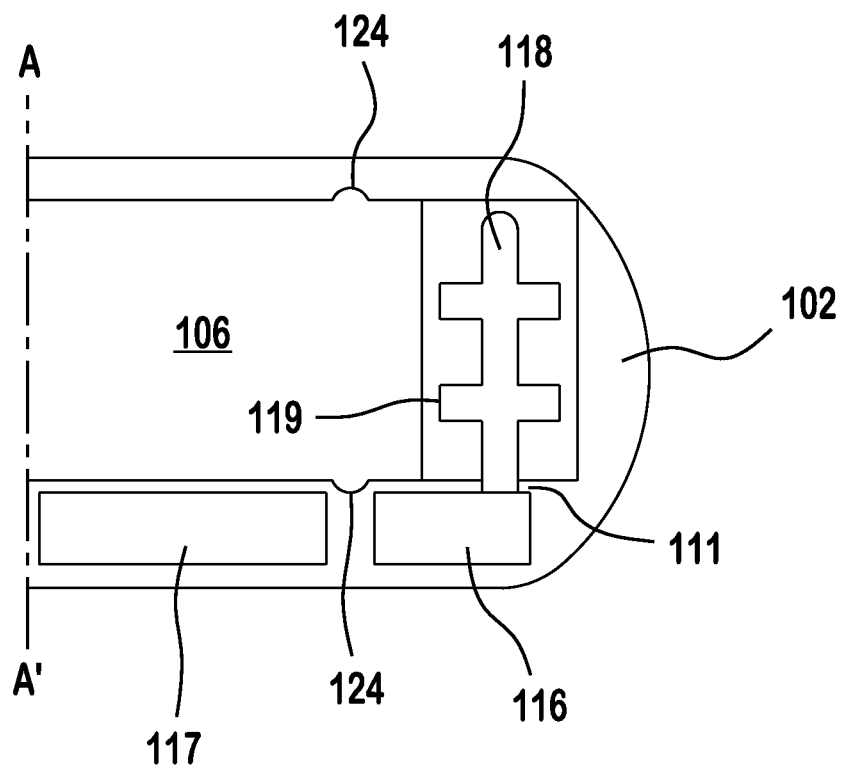
FIG. 5 is a top plan view of the reusable hub housing of FIG. 2.

FIG. 4 is an exploded perspective view of the insulin infusion pump 20 of FIG. 2 showing several components of the reusable hub 102 and the cartridge 108. Cartridge 108 includes a cartridge body 150, a cavity 152, a raised lip 126, a plastic plate 127, a plunger rubber 128 and a silicone plug 156. The components of the reusable hub housing 102 shown in this view include a motor 116, a plastic cap 122, a geared drive shaft 118 with gear teeth 119, a flexible polymer tape 120 including holes 121 and rubber strips 123. FIG. 4 shows the main elements that comprise the drive system of the pump 20 according to the present invention. The exploded view clearly shows each of the individual elements and their interaction will be discussed herein.

Rubber plunger 128 wraps over plastic plate 127 substantially surrounding the plate 127 on one side, leaving the underside free to removably connect with cap 122 of the reusable hub 102. As the rubber plunger 128 substantially covers plate 127, the term plunger 128 will be used throughout to encompass both the plate 127 and rubber 128. During use, plug 156 may be situated at the dispensing tip 154 of the cartridge body 150 thereby providing a first seal at the distal end 112 of the cartridge 108. Rubber plunger 128 functions to form a second seal towards the proximal end 110 of the cartridge 108 when the cartridge is full of liquid. During use within the infusion pump, this second seal moves in a direction towards the distal end 112 of the cartridge 108 as the plunger 128 is driven into the cartridge in order to infuse liquid medication to the patient.

FIG. 4 shows gear teeth 119 located on drive shaft 118 and cooperating holes 121 located on the flexible drive tape 120 configured to receive gear teeth 119. Flexible drive tape 120 may be permanently attached to cap 122 at a first end 130 whilst the area of tape 120 between the first end 130 and the second end 140 (depicted in FIG. 7) wraps around geared drive shaft 118 enabling the series of holes 121, spaced nanometers apart, to mate up with cooperating gear teeth 119 on drive shaft 118. The interaction of gear teeth 119 with holes 121 provide the traction for driving tape 120 in both a forwards and backwards direction when driven by motor 116. The combination of flexible drive tape 120, geared drive shaft 118 and piezoelectric motor 116 functions together to provide a reliable, tightly regulated liquid infusion system according to the present invention.

Several different methods are available for patterning structures such as holes 121 on drive tape 120 in a submicron resolution including but not restricted to, chemical stamping, laser micro patterning or lithography for example.

Motor 116 may be a small stepping rotational piezoelectric motor such as the 'Blé' or 'Sicher' available from Miniswys Piezomotors, Biel, Switzerland. Commercially available piezoelectric motors have the ability to make very fine steps, providing precision on the nanometer scale. Motor 116 drives geared drive shaft 118 in order to advance and/or retract the flexible drive tape 120 that in turn advances or retracts the plunger within the cartridge 108. As the drive tape 120 is permanently attached to cap 122, which is in turn connected to plunger 128 when a cartridge is present, then forwards and backwards movements of drive tape 120 simultaneously acts upon the plunger 128 driving it either into or out of the cartridge 108. Incremental forward movements of the plunger 128 into cartridge 108 functions to dispense defined quantities of insulin into the patient via an infusion set.

In one embodiment it is intended that a user would be able to access the infusion pump 20 in order to remove and replace a cartridge 108 once spent. The infusion set and the cartridge may not be reusable but the hub housing 102 of FIG. 3 and its internal components may be. Cartridge 108 may simply unsnap at the interface between cap 122 and the plastic plate 127 component of plunger 128 as previously described. Optionally the user may remove the entire infusion pump or patch pump 20. In one embodiment, a new, full cartridge 108 may be inserted into the reusable hub 102 by first inserting proximal end 110 i.e. plunger 128 end first, until the lip 126 snaps into cooperating groove 124. Simultaneously, plate 127 on the underside of the plunger 128 snaps into plastic cap 122 that is permanently attached to the first end 130 of the flexible drive tape 120. In another example embodiment, all or part of the liquid infusion system may be disposable.

FIG. 5 is a top plan view of the reusable hub housing 102 of FIG. 2, showing a recess or cavity 106 adapted to receive the cartridge 108 of FIGS. 2, 4, 8 and 9 to 12. In one embodiment raised lip 126 on cartridge 108 slots or clips into corresponding groove or recess 124. Geared drive shaft 118 includes small pegs or teeth 119 that engage with corresponding holes 121 in drive tape 120 (as shown in FIG. 4). Geared drive shaft is driven by motor 116 following instruction from electrical components 117. Optionally, pump 20 may be operated via a remote device 10, such as a handheld blood glucose monitoring meter for example, that communicates with electrical components 117. Pump 20 may include a seal 111 between the geared drive shaft 118 and the motor 116 to virtually eliminate the possibility of fluids such as water entering the pump when worn by the user.

FIG. 6 shows a side plan view of the reusable hub housing of FIGS. 2, 3 and 5, including many of the same elements as previously described. In addition FIG. 6 includes an example embodiment of a recess or cavity 115 that functions to receive flexible drive tape 120 when retracted out-with the cartridge 108. FIG. 6 also includes an optional seal 113 located around the tape. Seal 113 functions to ensure the pump is watertight as well as acting to minimize the risk of substances or particles entering into the working components of the pump, particularly whilst the user has the reusable hub 102 open during the process of replacing the cartridge 108.

In an example embodiment, the compartment containing the flexible tape 120 and the drive shaft 118 may be completely sealed off from the motor 116 configured to drive the geared drive shaft 118 by action of seal 111. Additionally there may be a further seal 113 through which the flexible tape 120 travels in order to separate the tape 120 from the cartridge 108. Plastic cap 122 and cooperating grommets function to keep the reusable hub 102 sealed when there is no cartridge present. Optionally, the reusable hub 102 may be completely sealed to prevent any contaminants entering the mechanism whilst the access hatch is open. Sealing the hub portion 102 also prevents the user from having any visibility of, or access to the components that are critical to the operation of the liquid infusion system. Use of a sealed, reusable hub 102 enables the user to easily and intuitively remove a spent cartridge and insert a new, full one, without having to interact with other components or undertake additional steps such as feeding the tape between guide rollers for example.

Figure 7:
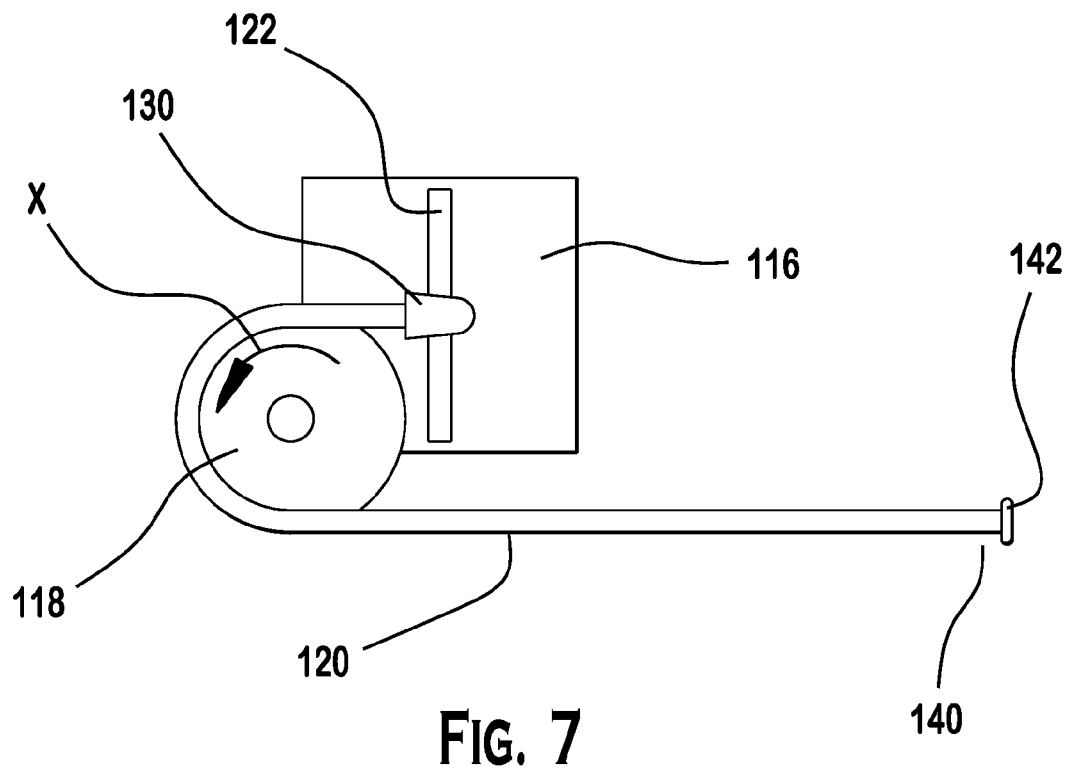
FIG. 7 is a simplified side plan view of the reusable hub portion of FIGS. 2 and 4.

FIG. 7 is a further, simplified side-plan view showing the main drive components of the reusable hub housing 102 of FIGS. 2 and 3, including a motor 116, a geared drive shaft 118, a cap 122 and a flexible drive tape 120 having a first end 130 and a second end 140 with a stop element 142. Arrow 'X' indicates the direction of rotation of geared drive shaft 118 to fully retract drive tape 120 to allow replacement of a spent cartridge 108.

FIG. 7 shows a flexible drive tape 120 having a first end 130 and a second end 140, and may comprise of a thin, flexible polymer material such as Polyethylene for example, or may be a flat metal alloy such as those produced by EtchLogic, Attleboro, USA. The flexible drive tape 120 may be a striated polymer, being flexible only along its longitudinal axis i.e. in a direction parallel to the length of the tape 120, and not being flexible along its shorter axis i.e. parallel to its width. First end 130 of the flexible drive tape 120 may be permanently attached to a cap 122, and second end 140 of the drive tape 120 may be free from restraint or alternatively it may be fixed at a certain point. Optionally, flexible tape 120 may include additional rubber strips 123 (seen in FIG. 6) along its edges in order for the drive tape 120 to fit snuggly against the internal walls of cartridge 108. Strips 123 provide support and rigidity to drive tape 120, as well as interacting with the geometrical shape of cartridge body 150 to ensure reliable movement of tape 120 within the cartridge 108, as will be discussed in more detail in relation to FIGS. 11a, 11b, and 11c. Flexible drive tape 120 may only be able to advance into cartridge 108 to a defined maximum distance determined by activation of stop element 142 at second end 140 of the drive tape 120.

Conventional cartridges or syringes generally operate by having a piston rod to force the piston into the cartridge to infuse the liquid to the patient. Such a piston rod may be made of a flexible but typically incompressible material, such as thin metal or hard plastic for example. Some conventional systems incorporate a flexible helix and rely upon accurate dimensions in order to transmit a certain axial pressing force without bending out as this could result in imprecise dosage. According to the present invention, the interaction of flexible drive tape 120, rubber strips 123 and the specific cartridge geometry provides a reliable longitudinal displacement within the cartridge, which cooperate with the geared drive shaft 118 and piezoelectric motor 116 to provide a space-efficient and tightly regulated dosing system, as will be described further herein. Flexible drive tape 120 provides a space-efficient advantage by functioning to securely wrap around the circumference of geared drive shaft 118, positioned immediately at the base of the cartridge 108, consuming a tightly curved path of 180 degrees and taking up a position either above or below the cartridge 108 once driven outside of the cartridge, as shown and described in relation to FIG. 6. Drive tape 120 extends along the length of the cartridge 108, located between the cartridge and the wall of the reusable hub housing 102.

FIG. 2 shows drive tape 120 engaged with geared drive shaft 118 and wrapping behind cartridge 108 (obscured from view). FIG. 7 shows the second end 140 of drive tape 120 wrapped below where a cartridge would be located during use, however it would be apparent to a person skilled in the art that the cartridge may be used in any orientation and therefore the second end of the flexible drive tape 120 may wrap above the cartridge, or be contained within a specifically designed slot at any position within hub housing 102, once retracted out-with the cartridge.

The ability of the flexible drive tape 120 to wrap around the geared drive shaft 118 immediately at the base of cartridge 108, combined with the geometry of the cartridge provides an advantageous space-efficient liquid infusion system according to the present invention, as will be described further in relation to FIGS. 11a, 11b, 11c and FIG. 12.

Refraction of the plunger 128 out of the cavity of the cartridge 108, as shown in FIG. 2, allows for removal of a spent cartridge and replacement of a new, full one. In order to remove and replace a cartridge 108, flexible drive tape 120 must be in a fully refracted position such as that shown in FIGS. 2 and 7. When cap 122 is attached to the plunger 128 of a cartridge 108, retracting drive tape 120 simultaneously pulls cap 122 and plunger 128 in the direction towards geared drive shaft 118, indicated by arrow 'X' in FIG. 4. Cap 122 comes to rest close to geared drive shaft 118 slightly outside of cartridge 108, allowing the plunger 128 of cartridge 108 to be disconnected from cap 122.

Figure 8:
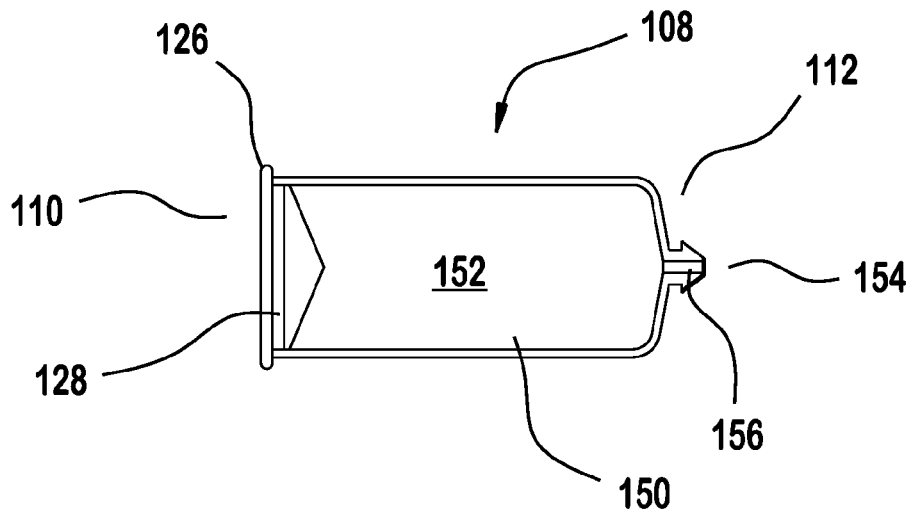
FIG. 8 is a side plan view of the cartridge of FIGS. 2 and 4.

FIG. 8 is a side plan view of the cartridge 108 of FIG. 2 including a cartridge body 150 having a proximal end 110, a distal end 112 and a cavity 152 therein. Proximal end 110 includes a molded lip 126 and distal end 112 includes a dispensing tip 154 and a plug 156. When the cavity 152 of cartridge 108 is full with a medicinal liquid such as insulin for example, then plunger 128 is located towards the cartridge proximal end 110.

Plug 156 may be formed of a resilient, deformable material such as silicone for example. Unless pierced, plug 156 acts to close or seal the dispensing tip 154 of cartridge 108 through which insulin is transferred to the patient typically via an infusion set. When the cartridge 108 is full of a liquid such as insulin, plunger 128 forms a seal at the proximal end 110. Plunger 128 is likely to comprise of a resilient, deformable rubber wrapped around a hard plastic plate 127 (seen in FIG. 4) that is flush with the outermost face of the rubber plunger 128. The hard plastic plate 127 provides additional strength and rigidity to the rubber plunger 128 as it is driven both forwards and backwards within the cartridge cavity 152. Plug 156 and rubber plunger 128 function to provide two barriers whereby the cartridge cavity 152 can only be accessed if the silicone plug 156 is pierced with a hollow needle.

During use, a patient would either receive new cartridges already filled with insulin, or alternatively the patient would have to fill a new, sterile cartridge with insulin prior to use of the pump system. To fill a cartridge, the patient would require a hypodermic needle that typically snaps on and off the tip 154 of the cartridge 108. While snapped on, the back end of this needle would pierce the silicone plug 156 thereby penetrating the seal and opening the tip of the cartridge. In addition, a hard plastic plunger (not shown) that is slightly longer in length than the cartridge body 150 is also required and snaps on the hard plastic plate 127 on the underside of the rubber plunger 128. The hypodermic needle and plastic plunger allow the user to fill the cartridge with insulin as they would any other syringe. After the cartridge is filled, the user is able to remove and discard the hypodermic needle and plunger, leaving them with a filled cartridge ready to be inserted into the pump 20.

In order to use any type of insulin pump system, a user typically has to first insert an infusion set into their skin. Many different types of infusion sets are commercially available and will therefore not be described further herein. It is intended that cooperation with an infusion set, such as that shown and described in relation to FIG. 3b, does not significantly increase the size of the pump 20 due to specifically designed grooves on the underside of the pump, designed to receive the infusion set thereby allowing the pump 20 to lie flush with the skin. The end of the infusion set may pierce the cartridge 108 and also seal the remaining opening in the hub housing 102, snapping together, completely sealing the system and opening the cartridge to the body.

Figure 9:
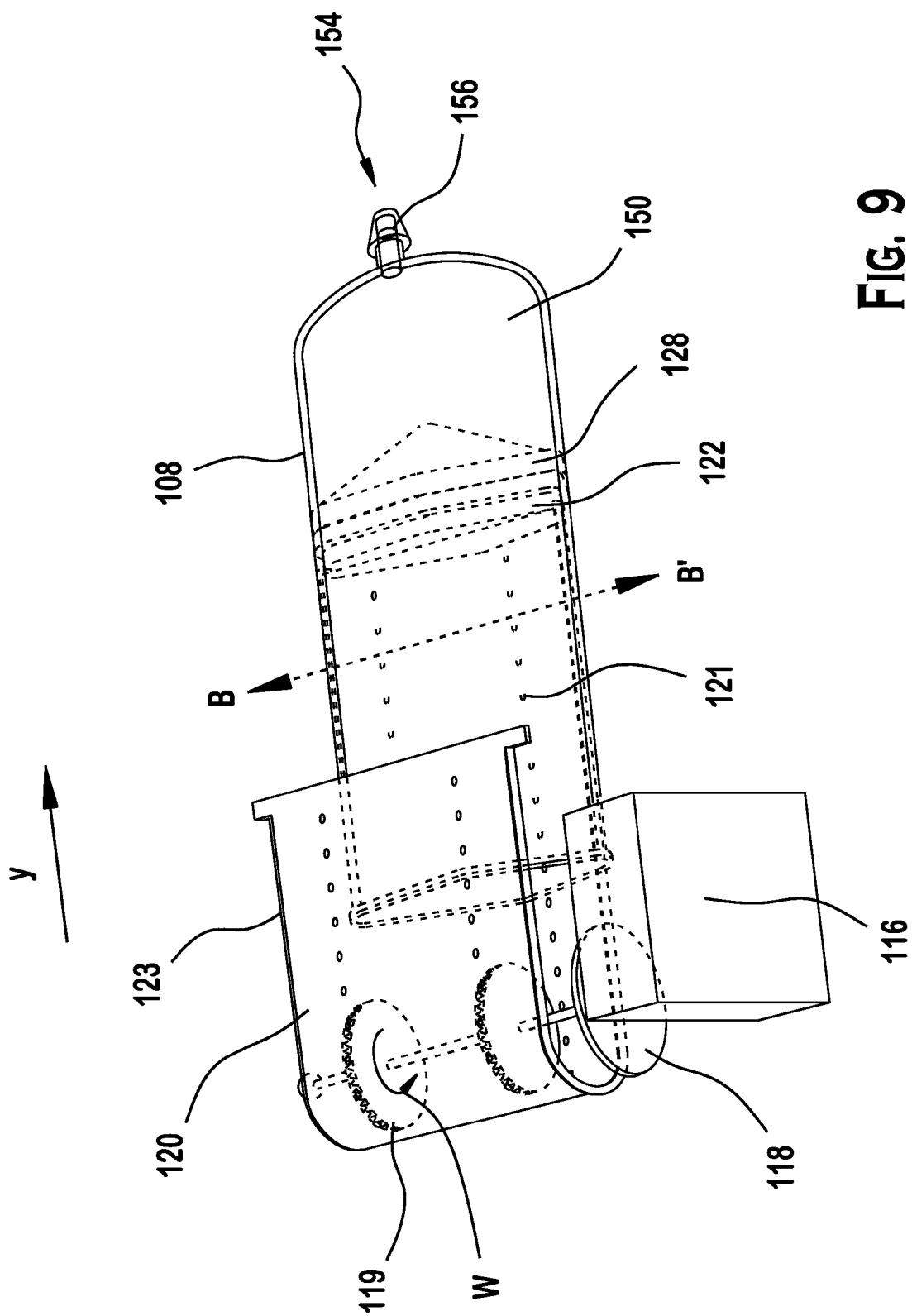
FIG. 9 is a perspective view of the pump of FIGS. 2 to 6 showing the plunger in an advanced position within the cartridge body.
Figure 10:
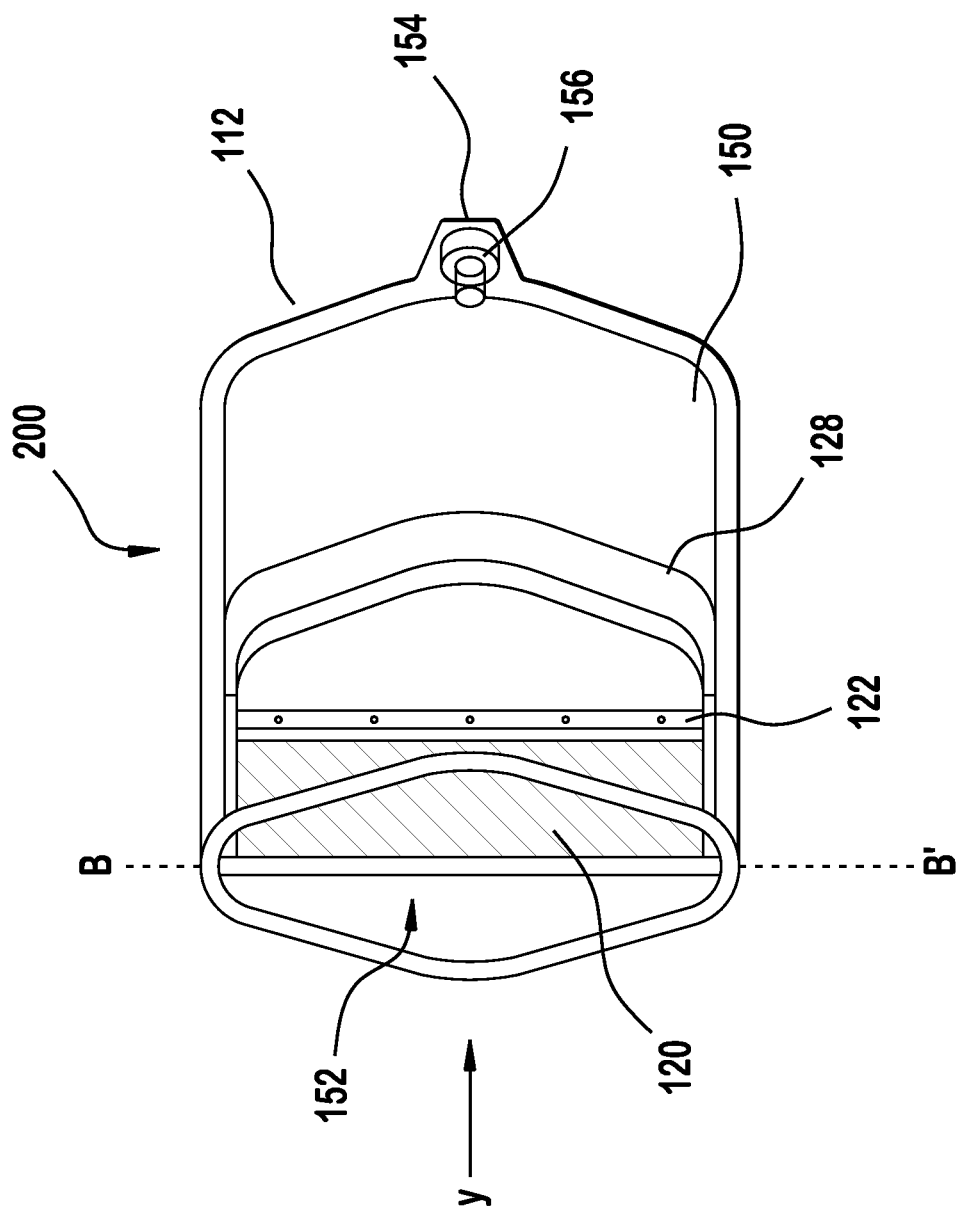
FIG. 10 is a close-up cross-sectional view of the cartridge of FIG. 9.

FIG. 9 is a perspective view of the liquid infusion pump 20 of FIGS. 2 to 8 including a cartridge body 150 with a dispensing tip 154 and a plug 156, a rubber plunger 128, a motor 116, a geared drive shaft 118 with teeth 119, a flexible drive tape 120 with holes 121 and support ribs 123. FIG. 7 also shows a cross section B-B' through which the view of FIG. 10 is seen when viewed in a direction depicted by arrow Y. Arrow 'W' indicates the direction of rotation of drive shaft 118 in order to advance plunger 128 into the cavity 152 of cartridge 108.

FIG. 10 is a close-up cross-sectional view of the cartridge of FIG. 9 seen through line B-B' from a direction indicated by arrow Y in FIG. 9. Cross section 200 shows the distal end 112 of cartridge 108 with a cartridge body 150, a cavity 152, a dispensing tip 154 and a plug 156. Flexible polymer tape 120 is shown attached to a plastic cap 122 and plunger rubber 128.

Referring now to FIGS. 9 and 10, cartridge body 150 has been illustrated as semi-transparent for the purpose of allowing the plunger 128 to be seen as it is driven into cavity 152 of cartridge 108. Both FIGS. 9 and 10 show the plunger 128 now in a more advanced position within the cartridge body 108. FIG. 9 shows teeth 119 on the geared drive shaft 118 permanently engaged with a series of nano-scale holes 121 spaced nanometers apart on drive tape 120. It is not intended that teeth 119 become completely disengaged from holes 121 at any point. Following instruction from the handheld device 10, motor 116 turns geared drive shaft 118 in a direction indicated by arrow 'W' whereby teeth 119 and holes 121 interact to drive the flexible drive tape 120 into cartridge 108 and subsequently pushing plunger 128 forwards by a predetermined increment to dose the correct amount of insulin to the user via an infusion set.

The cooperation of teeth 119 with holes 121 as well as the ability of motor 116 to work on the nano-scale level, thereby provide a reliable infusion drive system having tight dose regulation enabling small incremental quantities of liquid medication to be dispensed from the cartridge and transferred to a patient via an infusion set following instruction via the handheld device 10.

Line B-B' shows a cross-section through which the view of FIG. 10 is seen. FIG. 10 shows a close-up view of the geometry of the cartridge body 150, and the channel in which drive tape 120 has restricted movement. As described earlier, and will be described in further detail in relation to FIGS. 11a, 11b and 11c, the geometry of cartridge body 150 is specifically designed to ensure drive tape 120 can only move longitudinally i.e. backwards and forwards in the direction parallel to the length of cartridge 108. Drive tape 120 is substantially prevented from any axial movement. Showing cartridge body 150 as semi-transparent in FIGS. 9 and 10 allows the close fit of plunger 128 within cartridge 108 to be seen. As plunger 128 advances within the cartridge it acts as a movable seal, gliding against the internal walls of cartridge body 150 thereby forcing the required volume of liquid out through dispensing tip 154. Plunger 128, plate 127 and cap 122 are also therefore shaped to fit neatly within the cavity 152 of the cartridge 108, as will be described in further detail in relation to FIGS. 11a, 11b and 11c.

Figure 11B:
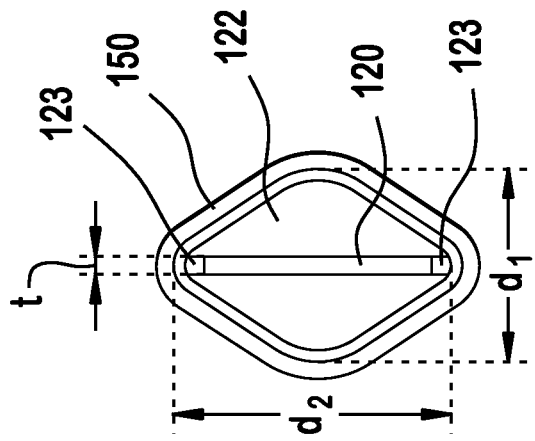
FIG. 11b is a cross-sectional view through the cartridge of FIGS. 9 and 10.
Figure 11A:
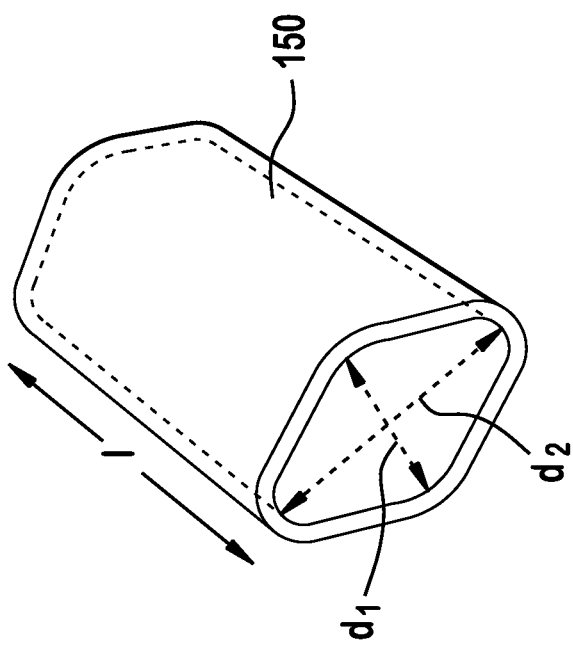
FIG. 11a is a perspective view of the cartridge body of FIGS. 2, 4, 9 and 10.

FIG. 11a shows a perspective view of the cartridge body 150 of FIGS. 2, 4, 9 and 10, including a length 'l', a first diameter '$d_1$' and a second diameter '$d_2$'.

FIG. 11a shows a semi-transparent view of the cartridge body 150 having a length 'l' in the range of approximately 2 to 5 cm (preferably closer to 3 cm), a first smaller diameter '$d_1$' in the range 0.5 to 2 cm (preferably closer to 1 cm) and a second diameter '$d_2$' in the range 1 to 3 cm (preferably closer to 1.46 cm). Cartridge body 150 may be made of polypropylene for example and is typically molded in a single piece with a wall thickness approximately in the range 1 to 3 mm. In one embodiment, cartridge body 150 comprises a substantially tubular vessel along its longer axis, parallel to its length 'l'. Across the shorter axis, parallel to its width, cartridge body 150 is approximately elliptical in shape as described in more detail in relation to FIG. 11c.

FIG. 11b shows a cross-sectional plan view of the cartridge body 150 of FIGS. 9 and 10 seen through line B-B' from the direction indicated by arrow 'Y'. FIG. 11b shows the cartridge having a first diameter '$d_1$' and a second diameter '$d_2$' as shown in FIG. 11a. FIG. 11b also includes a cap 122 and a flexible drive tape 120 with a thickness T.

The cross-sectional top plan view of FIG. 11b shows a section through the cartridge 108 of FIG. 10 when viewed from the direction indicated by arrow 'Y'. The cross-section shows flexible drive tape 120 with rubber edging 123 fitting neatly within the cavity of cartridge body 150, in an orientation in line with second diameter '$d_2$'. Diameter '$d_2$' corresponds to the largest internal diameter of the substantially elliptical cross-section of cartridge body 150, and diameter '$d_2$' corresponds to the smallest diameter. Diameters $d_1$ and $d_2$ are substantially perpendicular to one another. Diameter '$d_2$' thereby provides a single 'channel' with the only dimension large enough to accommodate drive tape 120 and hence restricting its movement to within this single orientation.

Cap 122 and plunger 128 exhibit the same substantially elliptical shape as the cross-section of cartridge body 150, and therefore fit snugly therein. Cap 122 interacts with plunger 128 functioning as a moving seal against the internal walls of the cartridge body 150 during use, ensuring that the liquid is reliably held with the cavity 152 of cartridge 108. Rubber edges or ribs 123 also contact the internal walls of the cartridge body as the drive tape 120 is driven both backwards and forwards within the cartridge, thereby providing structural rigidity and ensuring a secure fit of drive tape 120 in the single channel provided by diameter '$d_2$'. The geometry of cartridge body 150 is specifically designed to restrain movement of drive tape 120, thereby limiting movement to within a longitudinal direction i.e. parallel to the length of the cartridge 108. Drive tape 120 is not permitted to flex, rotate or move by any substantial amount in an axial direction i.e. parallel to the width of cartridge body 150.

Figure 11C:
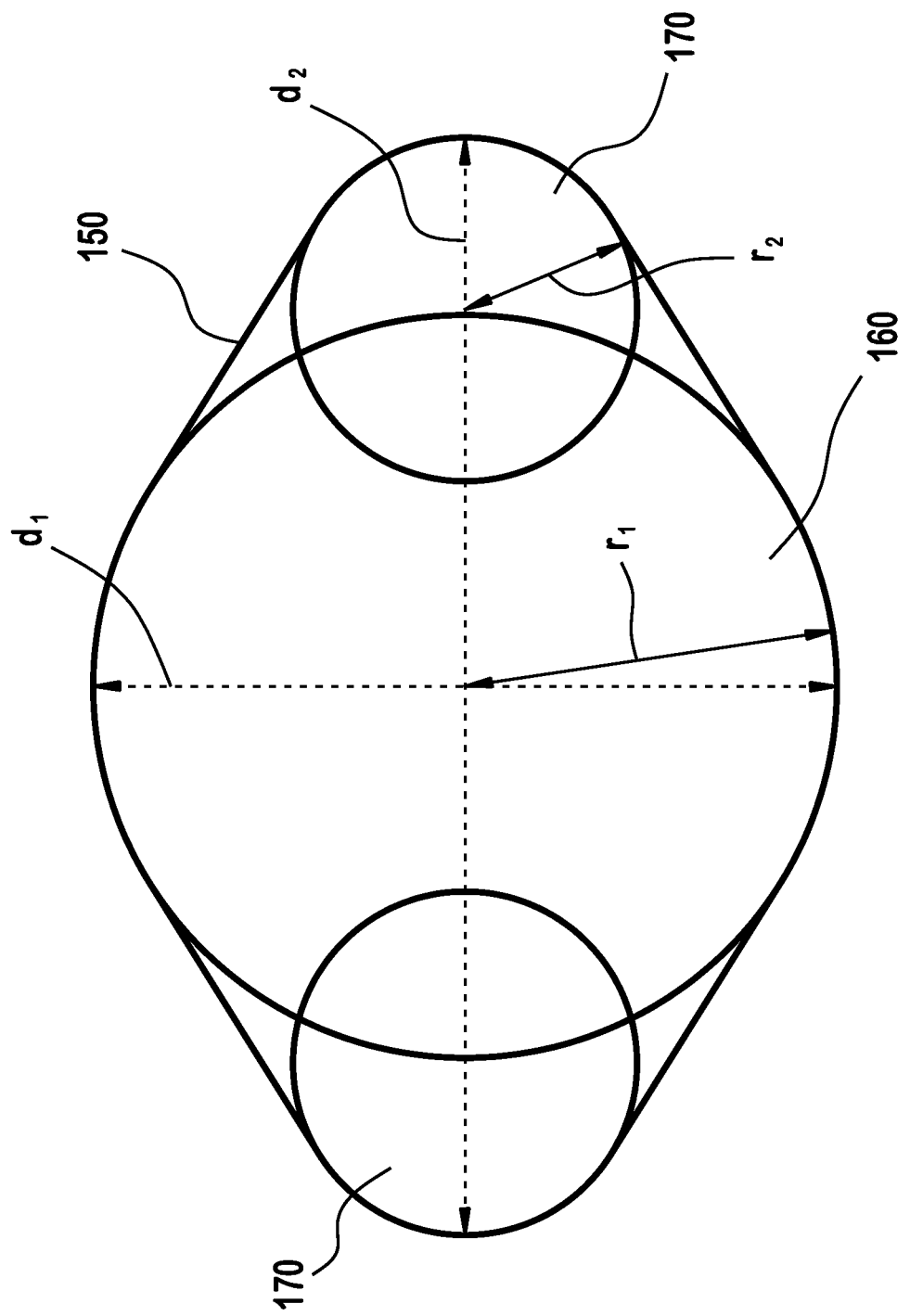
FIG. 11c is a schematic view of the geometrical make-up of the cartridge body of FIGS. 11a and 11b.

FIG. 11c is a schematic view showing the same cross-section through cartridge body 150 as shown in FIG. 11b, depicting an example embodiment of the geometrical make-up of cartridge body 150, including a first diameter '$d_1$' and a second diameter '$d_2$', a large circle 160 with a radius $r_1$ and two smaller circles 170 each with a radius '$r_2$'.

The substantially elliptical shape of the cross-section of cartridge body 150 can be described geometrically as comprising a first large circle 160 with diameter '$d_1$' as discussed previously and a radius '$r_1$', and two smaller circles 170 each having a radius '$r_2$'. Radius '$r_1$' may be in the range 2 to 8 mm (more preferably closer to 5 mm), and radius '$r_2$' may be in the range 1 to 5 mm (more preferably closer to 2.3 mm). Placing the central point of one small circle 170 on the circumference of the larger circle 160, and placing the second small circle 170 in a similar position on the circumference of the large circle 160 directly opposite the first small circle, then a tangential line leaving the large circle 160 and drawn to encompass the two small circles provides the substantially elliptical geometry of the cartridge body 150 of the present invention.

It follows from the unique geometry of cartridge body 150 that cooperating elements such as rubber plunger 128, plastic plate 127 and cap 122 may also take on the same unique geometry in order to be able to fit securely to the inner circumference of the cartridge body 150 and form a seal to ensure that liquid held within cartridge 108 remains reliably within the cavity until dispensed. Furthermore, the secure fit of cap 122 and rubber plunger 128 (including plastic plate 127) within cartridge body 150 must also permit these components to advance and retract within the cavity of cartridge body 150 when driven by the motor 116.

This cross-sectional geometry of the cartridge body 150 not only provides a one-dimensional channel in which the flexible tape 120 can travel, but it also reduces the overall profile of the infusion system. A substantially elliptical shaped cartridge has a slightly more slender profile than conventional styles that are typically cylindrical. Discretion is typically important to patients who wear any type of medicinal pump, therefore the geometry of the cartridge 108 according to the present invention provides an important advantage in reducing the size of the profile of the infusion system. Incorporating the cartridge 108 and novel drive system of the present invention within a patch-pump for example, permits the dimensions of the system to be reduced substantially from those of a more conventional pump system (approximately 2.2 cm×5 cm×8 cm) to an overall profile closer to 1.5 cm×4 cm×4 cm, optionally with sloping or tapered sides in order to create two organic surfaces, a top and a bottom opposed to the "box" shape that is dimensioned. Such a patch pump can be worn extremely discreetly by the patient, potentially minimizing any inhibitions users may have about being tethered to a pump and therefore increasing overall confidence in the system potentially leading to better disease management.

Although a cartridge with substantially elliptical geometry is described herein, it would be apparent to a person skilled in the art that cartridges possessing different geometries may also be used in accordance with the present invention, and therefore such other geometries are intended to be included.

Figure 12:
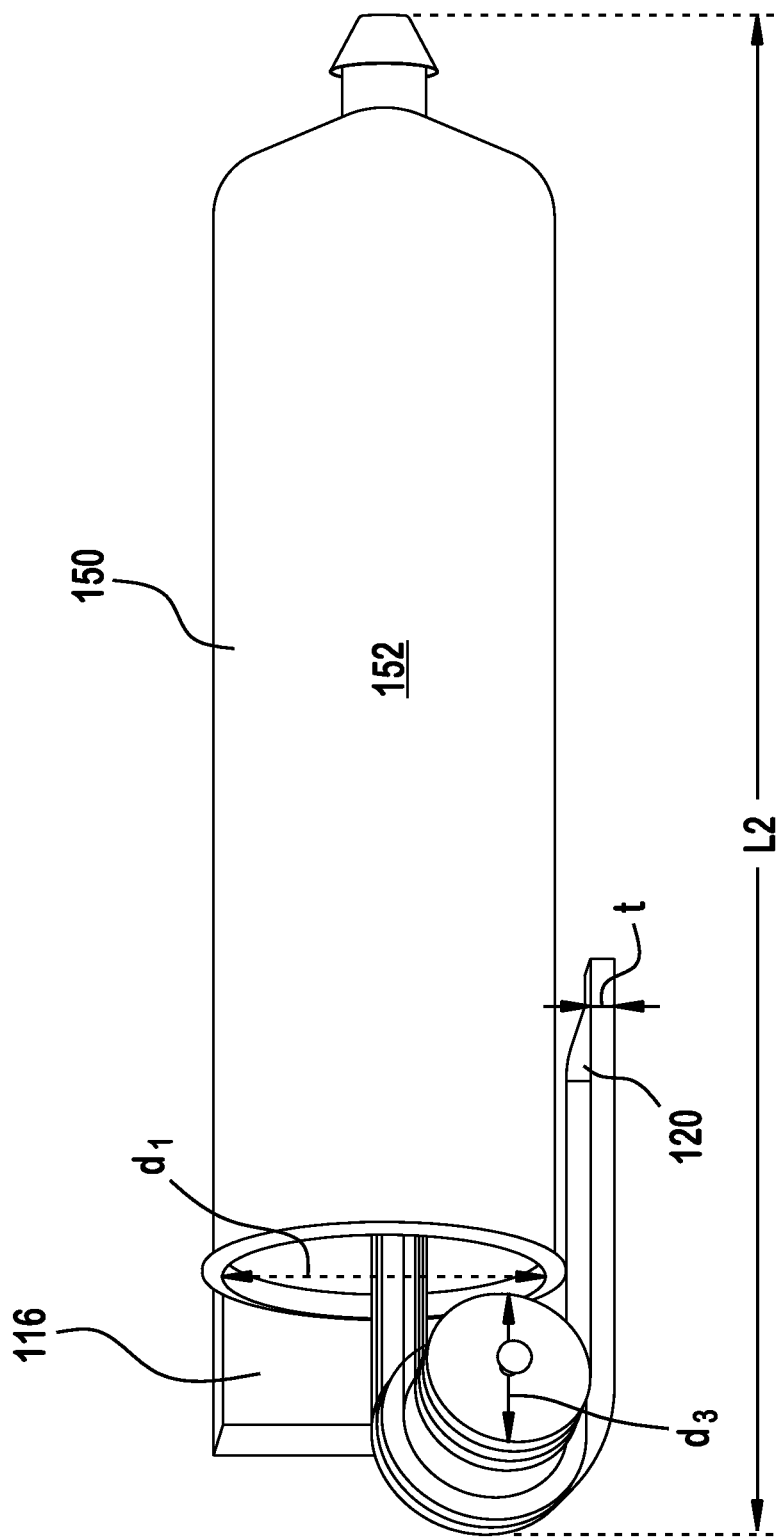
FIG. 12 is a perspective side view of the drive system of the pump shown in FIG. 2.

FIG. 12 is a perspective side view of the insulin infusion pump 20 of FIG. 2 including a cartridge body 150 with a cavity 152 and a small diameter '$d_1$', a motor 116, a drive tape 120 with a thickness 't' wrapped around a geared drive shaft 118 having a diameter '$d_3$'. FIG. 12 also shows a system length L2'.

Conventional commercially available cartridges (also known as syringes) typically require a total length 'L1' of at least twice the length of the cartridge body in order to be able to fully retract the typically incompressible plunger and completely fill the cavity of the cartridge with a liquid to be subsequently dispensed. In an embodiment of the present invention, the flexible drive tape 120 which both advances and retracts the plunger 128, has the ability to bend and wrap either above or below the cartridge 108 (whilst outside of the cartridge cavity 152) allowing the total length of the cartridge 12' to decrease below the convention described above as 11'. FIG. 12 shows the drive tape 120 wrapping below the cartridge, concealed from the user in a space provided between the cartridge 108 and the external housing 102 of the pump 20, as shown in FIG. 2.

According to the present invention, length 'L2' of the infusion system would be close to the sum of the length 'l' of the cartridge, plus the thickness T of the thin drive tape 120 plus the diameter '$d_3$' of geared drive shaft 118. In one example embodiment, diameter '$d_3$' may be approximately equal to half of the smallest diameter '$d_1$' of the cartridge 108. Total length L2 may therefore be described as:

$$L_2 = \sum \left( l + t + \frac{d_1}{2} \right)$$

This beneficial ratio would continue to improve with increasing cartridge length 'l' i.e. with use of larger capacity cartridges or syringes. This would allow support of larger cartridge volumes still within a small, compact and discreet infusion system. Often a limiting factor placed on pump users is the small size of the liquid cartridge that can be used with the pump, therefore the present invention aims to reduce this limitation.

A further advantage of the infusion system of the present invention is its ability to provide controlled infusion of a medicinal liquid. According to the present invention, a minimum infusion volume i.e. the smallest increment of the drive system may be in the region of approximately 0.00005 to 0.0002 units, and preferably more closer to 0.0001 units. The novel drive system of the present invention utilizes a flexible drive tape in cooperation with a geared drive shaft and piezo-electric motor to reliably infuse defined quantities of liquid medication to the user. The volume of the smallest dose increment may be determined by the combined interaction between series of holes 121 on drive tape 120, gear teeth 119 on drive shaft 118 and motor 116. According to the present invention, series of holes 121 may be spaced nanometers apart, and use of a piezoelectric motor 116 provides the ability to operate on the nano-scale level. Therefore, any increase in the size of the cartridge 108 used for example, would not affect the minimum dose increment. The infusion system of the present invention may be used with virtually any size of cartridge, whilst maintaining a small and compact system.

The reusable hub is an enclosed module, where the components are sealed and optionally invisible to the user, therefore the ease of cartridge replacement has many advantages over other systems known in the art that require additional user steps such as feeding the drive tape between capstan and pinch rollers prior to reconnecting it to the piston for example. The system disclosed herein enables the user to very easily and intuitively replace a spent cartridge for a new, full cartridge simply by opening the external housing of the pump, lifting out the spent cartridge and replacing this with a new one, ensuring that it slots and securely 'clicks' into position. The user would then close the pump housing triggering the motor to activate the plunger thereby priming the system for use.

Furthermore, the drive system described herein is particularly space-efficient in that the profile of the pump may be approximately equal to the length of the cartridge plus the thickness of the drive tape plus the diameter of the geared drive shaft. Where the diameter of the geared drive shaft may be approximately equal to half the smallest diameter of the cartridge. The substantially elliptical geometry of the cartridge provides a space-efficient solution in both the length and width dimensions, as well as providing a single channel through which the flexible drive tape can be driven to reliably dispense the required amount of medication to the patient. Patients typically show preference for small, compact systems enabling them to manage their condition discreetly.

In addition, the reduced number of components ensures a more compact and easier to manufacture system when compared to infusion systems known in the art. Use of a thin, flexible drive tape, wrapped around a small-diameter drive shaft with relatively tight curvature, and stored between the cartridge and the device housing provides a space-efficient solution without additional components such as take-up spools, rollers, guides or lead screws. A motor driven system such as that disclosed herein may be advantageous over a fully mechanical system that may be subject to increased friction and wear.

A further advantage of the present invention is the use of a cartridge with substantially elliptical shaped geometry which provides a single channel at its widest diameter through which the plunger and drive tape have restricted travel. Such rotational restrictions on the movement of the plunger and drive tape ensure their reliable longitudinal displacement within the cartridge in order to achieve tight dose regulation of the liquid medication. Some infusion systems known in the art rely upon the longitudinal stiffness of curved spring steel for example, or prevention of a flexible helix from bending under compression; both of which may potentially introduce inaccuracy in the reliability of dose regulation.

A further advantage of the present invention is the ability of the infusion system described herein to virtually eliminate many of the limits currently placed on users by commercially available infusion configurations. Such limitations include, but are not limited to, the patient being tethered to a large, bulky device that they prefer to conceal under clothing but they may have to remove for use. Carrying multiple devices such as a separate pump and meter is a further limitation on users adding to inconvenience and therefore reduced motivation to monitor their blood glucose and manage their condition. Furthermore, the restriction on size of cartridge that the pump will accept e.g. typically a 200U cartridge can be a further limitation. The present invention aims to reduce or virtually eliminate many of the aforementioned problems. The present invention provides a small, discreet pump e.g. a patch pump that may be worn by a patient attached to their skin in a location such as the stomach area that can be discreet from others as well as being comfortable and convenient.

It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. A liquid infusion device, comprising:
   a flexible drive tape having a plurality of holes therethrough and aligned essentially linearly along the length of the drive tape, the plurality of holes spaced apart at a fixed increment, the flexible drive tape comprising a striated polymer, wherein the flexible tape drive is flexible in a longitudinal direction and rigid in an axial direction, and the flexible drive tape comprises at least one rubber strip disposed on each edge of a longitudinal axis of the flexible drive tape;
   a drive shaft comprising at least one gear, the at least one gear comprising a plurality of teeth that align and engage the holes in the flexible drive tape;
   a piezoelectric motor for advancing and retracting the flexible drive tape;
   a plunger attached to or in communication with at least one end of the flexible drive tape; and
   a cartridge having a substantially elliptical geometry for containing a liquid medication for receiving the plunger and expelling the liquid medication upon movement of the plunger in the cartridge and wherein elliptical geometry of the cartridge provides a single channel at its widest diameter through which the plunger and drive tape have restricted travel,
   wherein the piezoelectric motor turns the drive shaft and is configured for both advancing and retracting the flexible drive tape and, thereby, driving the plunger into or withdrawing the plunger out of the cartridge in an increment correlating to the fixed increment between holes.

* * * * *